United States Patent
Luo et al.

(10) Patent No.: US 9,392,956 B2
(45) Date of Patent: Jul. 19, 2016

(54) DRY SENSOR EEG/EMG AND MOTION SENSING SYSTEM FOR SEIZURE DETECTION AND MONITORING

(75) Inventors: An Luo, San Jose, CA (US); Cheng-I Chuang, San Jose, CA (US); Stanley Yang, San Jose, CA (US)

(73) Assignee: NeuroSky, Inc., San Jose, CA (US)

( * ) Notice: Subject to any disclaimer, the term of this patent is extended or adjusted under 35 U.S.C. 154(b) by 420 days.

(21) Appl. No.: 13/354,148

(22) Filed: Jan. 19, 2012

(65) Prior Publication Data

US 2012/0197092 A1 Aug. 2, 2012

Related U.S. Application Data

(60) Provisional application No. 61/437,403, filed on Jan. 28, 2011.

(51) Int. Cl.
| | |
|---|---|
| *A61B 5/04* | (2006.01) |
| *A61B 5/0492* | (2006.01) |
| *A61B 5/0478* | (2006.01) |
| *A61B 5/11* | (2006.01) |
| *A61B 5/00* | (2006.01) |

(52) U.S. Cl.
CPC ............ *A61B 5/0492* (2013.01); *A61B 5/0478* (2013.01); *A61B 5/11* (2013.01); *A61B 5/4094* (2013.01); *A61B 5/6803* (2013.01)

(58) Field of Classification Search
CPC ... A61B 5/0476; A61B 5/0478; A61B 5/6803
USPC .................................................. 600/544, 545
See application file for complete search history.

(56) References Cited

U.S. PATENT DOCUMENTS

| | | | |
|---|---|---|---|
| 8,337,404 B2* | 12/2012 | Osorio | ......................... 600/301 |
| 2001/0044573 A1 | 11/2001 | Manoli et al. | |
| 2001/0044579 A1 | 11/2001 | Pratt | |
| 2001/0050754 A1 | 12/2001 | Hay et al. | |
| 2004/0267152 A1 | 12/2004 | Pineda | |
| 2005/0165458 A1* | 7/2005 | Boveja et al. | ................... 607/45 |
| 2006/0094974 A1* | 5/2006 | Cain | ............................ 600/544 |

(Continued)

FOREIGN PATENT DOCUMENTS

| | | |
|---|---|---|
| CN | 101340846 | 1/2009 |
| JP | 2004-120049 | 4/2004 |

(Continued)

*Primary Examiner* — Christian Jang
(74) *Attorney, Agent, or Firm* — Van Pelt, Yi & James LLP

(57) ABSTRACT

A dry sensor EEG/EMG and motion sensing system for seizure detection and monitoring is disclosed. In some embodiments, a system for seizure detection/monitoring is provided that can measure a user's EEG/EMG and motor activity, automatically detect an epileptic seizure and perform actions, such as triggering an alarm and/or turning off the provoking stimulation. In some embodiments, a system for seizure detection/monitoring is provided that can be used to continuously monitor and store a user's EEG/EMG and motor activity for doctor evaluation. In some embodiments, a system for seizure detection/monitoring is provided that can be mounted directly on a user's head using active dry EEG sensors. In some embodiments, a system for seizure detection/monitoring is provided that can be mounted into/onto a pair of glasses (e.g., 3D glasses), and the user's eyes can be automatically covered by the glasses if a seizure is detected.

23 Claims, 5 Drawing Sheets

(56) References Cited

U.S. PATENT DOCUMENTS

| | | | |
|---|---|---|---|
| 2006/0111644 A1* | 5/2006 | Guttag et al. | 600/544 |
| 2008/0091089 A1 | 4/2008 | Guillory et al. | |
| 2008/0146958 A1* | 6/2008 | Guillory et al. | 600/544 |
| 2009/0062678 A1* | 3/2009 | Beck-Nielsen | 600/544 |
| 2009/0062696 A1 | 3/2009 | Nathan et al. | |
| 2009/0069787 A1* | 3/2009 | Estes et al. | 604/503 |
| 2009/0099627 A1 | 4/2009 | Molnar et al. | |

FOREIGN PATENT DOCUMENTS

| | | |
|---|---|---|
| TW | 201034625 | 10/2010 |
| WO | 2007124040 | 11/2001 |
| WO | 2007111728 | 10/2007 |
| WO | 2010075115 | 7/2010 |

* cited by examiner

DRY SENSOR EEG/EMG AND MOTION SENSING SYSTEM FOR SEIZURE DETECTION AND MONITORING

CROSS REFERENCE TO OTHER APPLICATIONS

This application claims priority to U.S. Provisional Patent Application No. 61/437,403, entitled DRY SENSOR EEG/EMG AND MOTION SENSING SYSTEM FOR SEIZURE DETECTION AND MONITORING, filed Jan. 28, 2011, which is incorporated herein by reference for all purposes.

BACKGROUND OF THE INVENTION

It is estimated that 50 million people have epilepsy worldwide. Among them, it is further estimated that over 30% do not have an effective seizure control even with the best available medications. A seizure can generally happen anytime, anywhere, and very often without predictive signs, which can be especially dangerous when the patient is alone.

BRIEF DESCRIPTION OF THE DRAWINGS

Various embodiments of the invention are disclosed in the following detailed description and the accompanying drawings.

DETAILED DESCRIPTION

Figure 1:
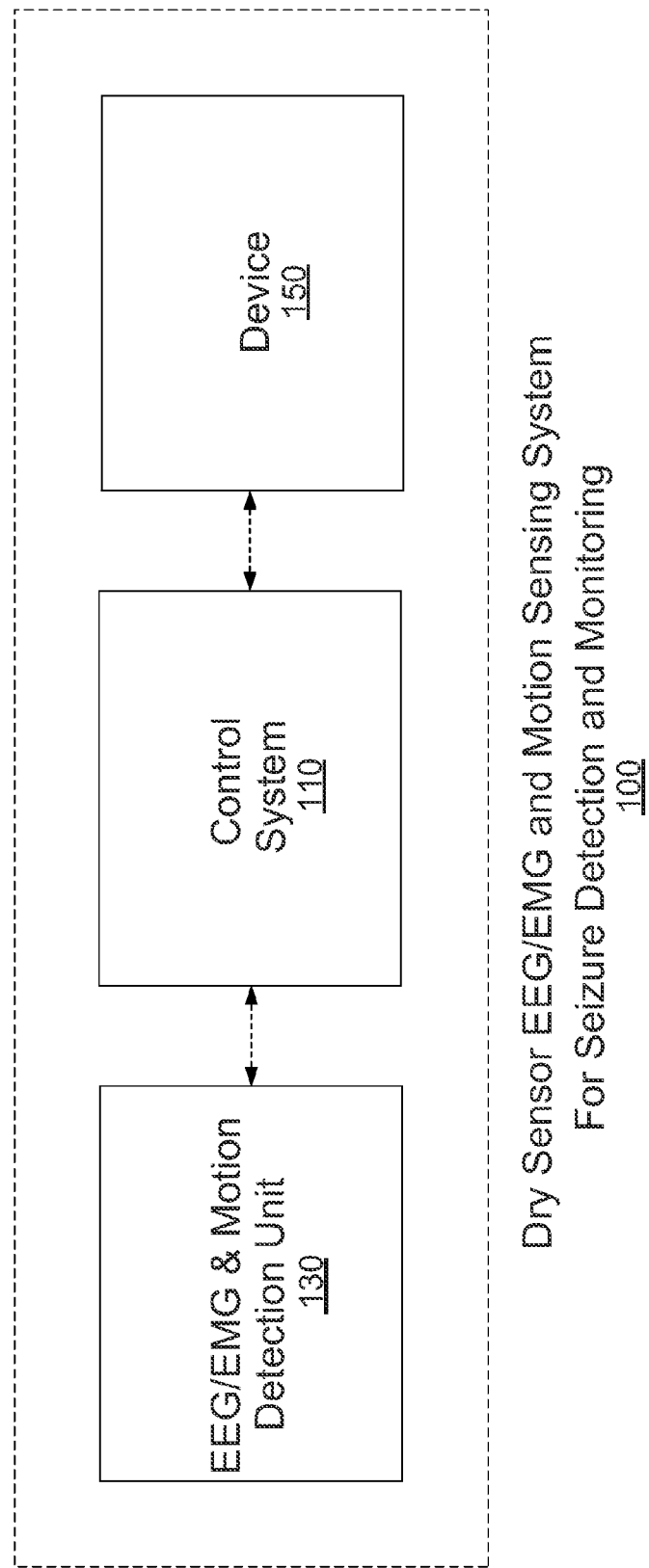
FIG. 1 is a block diagram illustrating a dry sensor EEG/EMG and motion sensing system for seizure detection and monitoring in accordance with some embodiments.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits (e.g., PCBs, ASICs, and/or FPGAs), and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

It is estimated that 50 million people have epilepsy worldwide. Among them, it is further estimated that over 30% do not have an effective seizure control even with the best available medications. A seizure can generally happen anytime, anywhere, and very often without predictive signs, which can be especially dangerous when the patient is alone.

Early detection of seizures can avoid further injuries and prevent long term damages to the patient's brain. Electroencephalography (EEG) monitoring is a primary tool to diagnose and evaluate epilepsy. Traditionally, EEG is recorded using medical grade EEG devices in epilepsy clinics. Before recording, a number of electrodes are typically glued to the patient's head using conductive gel. However, the application of conductive gel can require both a significant amount of time to apply to the patient's head (e.g., depending on the number of electrodes) and make the hair difficult to clean afterwards. Also, a brief recording of EEG at an epilepsy clinic will not capture the epileptic form EEG if the patient is not having a seizure at the moment or when he/she is not in seizure vulnerable period.

Specifically, when a patient is having a seizure or in a seizure vulnerable period, their EEG generally shows abnormal, excessive, or synchronous neuronal activity. If motor symptoms are present during a seizure, abnormal activity can also be detected by electromyography (EMG) or motion sensors. Automatic seizure detection systems exist that include one or more EEG and EMG sensors. However, conductive gel is needed for these EEG and EMG sensors. There are also approaches that use implantable seizure detection devices embedded underneath a patient's scalp, but these approaches are invasive and can often require a surgery to implant such seizure detection devices. Both the medical grade EEG sensors and the implantable EEG sensors are generally expensive and require assistance from professionals, and thus are difficult and/or impractical to use at home and/or on an everyday basis. Other automatic seizure detection systems employ motion, sound, and/or image sensors to monitor a patient's motor activity and transmit an alarm if seizures are detected.

In accordance with some embodiments, it is desirable to provide an automatic seizure detection system that is user friendly and economical (e.g., low cost). In accordance with some embodiments, it is also desirable to combine EEG/EMG sensing with motion sensing to provide for enhanced and more reliable seizure detection, and to store such time sensitive information for use and help in medical diagnosis and/or medical treatment.

More specifically, for patients with photosensitive epilepsy (PSE), seizures can be triggered by visual stimuli that form patterns in time or space, such as flashing lights, regular still or moving patterns. Television has traditionally been the most common source of seizures in PSE patients, for example, especially when the television is out of adjustment or is showing a rapidly flickering image. A common practice to stop or alleviate the seizure is to cover one or both patient's eyes. The advent of three dimensional (3D) movies and 3D televisions (e.g., which typically involves the use of special glasses for view such 3D content, referred to herein as 3D glasses) is also creating concerns regarding the effect of 3D viewing in triggering seizures.

In accordance with some embodiments, it is also desirable to embed an automatic seizure detection unit into/onto a pair of glasses, including, for example, 3D glasses. In some embodiments, a system for seizure detection/monitoring is provided that can measure a user's EEG/EMG and motor activity, automatically detect an epileptic seizure and perform actions, such as triggering an alarm and/or turning off the provoking stimulation. In some embodiments, a system for seizure detection/monitoring is provided that can be used to continuously monitor and store a user's EEG/EMG and motor activity for doctor evaluation. In some embodiments, a system for seizure detection/monitoring is provided that can be mounted directly on a user's head using active dry EEG sensors. In some embodiments, a system for seizure detection/monitoring is provided that can be mounted into/onto a pair of glasses (e.g., 3D glasses), and the user's eyes can be automatically covered by the glasses if a seizure is detected.

In some embodiments, a dry sensor EEG/EMG and motion sensing system for seizure detection and monitoring includes one or more dry EEG or EMG sensors mounted on a wearable object, a detection unit configured to determine a seizure event based on data received from the EEG or EMG sensor, and a transmission unit configured to send a seizure response. In some embodiments, a dry sensor EEG/EMG and motion sensing system for seizure detection and monitoring further includes any of a motion sensor, where the detection unit is configured to determine a seizure event based on data received from the EEG or EMG sensor and the motion sensor; a storage unit, where the storage unit is capable of recording seizure event data and non-seizure event data from the detection unit; and a location tracking unit. In some embodiments, the detection unit determines occurrence of a seizure based on a linear discrimination analysis, an artificial neural network, a decision tree, or a Bayesian method. In some embodiments, the wearable object is any of a headband, a pair of glasses, and a pair of active-lens 3D glasses. In some embodiments, a seizure response includes any of a trigger alarm communicated to a user or third party, commanding a device producing visual stimulus to modify its behavior, and administering treatment to a user.

FIG. 1 is a block diagram illustrating a dry sensor EEG/EMG and motion sensing system for seizure detection and monitoring in accordance with some embodiments. In some embodiments, for a dry sensor EEG/EMG and motion sensing system 100 for seizure detection and monitoring includes a control system 110, an EEG/EMG and motion detection unit 130, and a device 150. In some embodiments, the EEG/EMG and motion detection unit 130 includes one or more active dry EEG sensors and/or EMG sensors that can be placed on the forehead, scalp, and/or other areas of a patient/user. In some embodiments, the EEG/EMG and motion detection unit 130 includes a motion sensor (e.g., an accelerometer and/or other types of motion sensors). In some embodiments, a control system 110 for seizure detection/monitoring includes a motion sensing unit 120 that monitors a user's motor activity.

In some embodiments, the device 150 is included with or integrated with the dry sensor EEG/EMG and motion sensing system for seizure detection and monitoring 100, as shown, and communicates with the device 150 using a serial or other communication channel. In some embodiments, the device 150 is separate from the dry sensor EEG/EMG and motion sensing system for seizure detection and monitoring 100 and is in communication with the control system 110 using a wired line or wireless communication. In some embodiments, the control system 110 communicates with the EEG/EMG and motion detection unit 130 using a serial or other communication channel (e.g., wired or wireless).

In some embodiments, the EEG/EMG and motion detection unit 130 detects EEG and/or EMG signals of a user, and the control system 110 includes a processor configured to perform a seizure detection and monitoring algorithm for EEG and/or EMG signals detected by the EEG/EMG and motion detection unit 130 using various techniques as described herein.

In some embodiments, based on the seizure detection and monitoring determination(s), the control system 110 sends corresponding control signal(s) to the device 150 (e.g., for sending a communication or other notification to the patient/user, friends or family of the patient, medical or other professional support for the patient/user using various techniques described herein). In some embodiments, the EEG/EMG and motion detection unit 130 sends raw EEG/EMG signal data, or in some embodiments, processed EEG/EMG signal data (e.g., to filter out noise), to the control system 110 for further processing and/or analysis using various techniques described herein.

Figure 2:
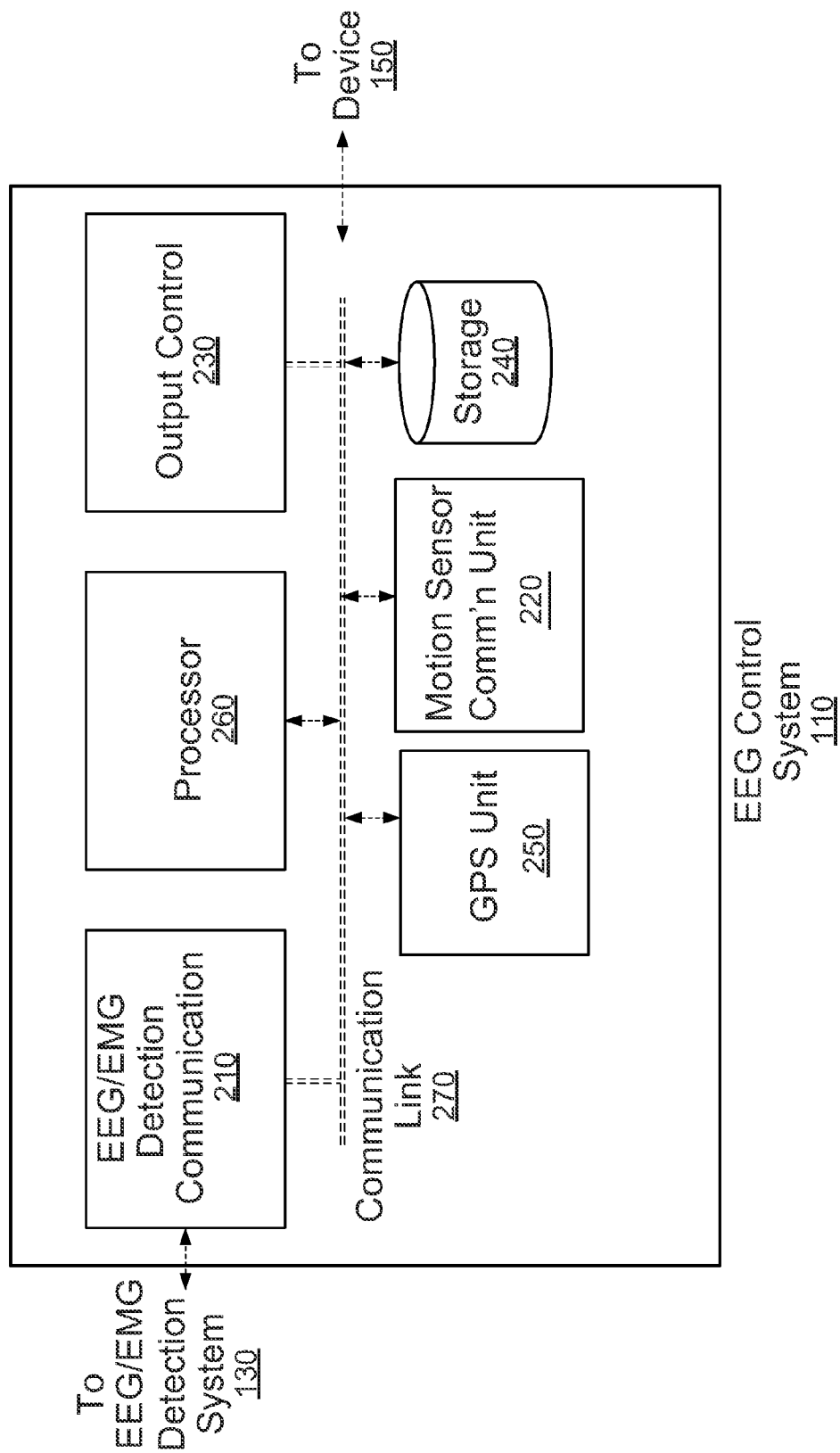
FIG. 2 is a functional diagram illustrating a control system for seizure detection and monitoring in accordance with some embodiments.

FIG. 2 is a block diagram illustrating a control system 110 for seizure detection and monitoring in accordance with some embodiments. In some embodiments, the control system 110 for seizure detection and monitoring includes, as shown, a dry sensor EEG/EMG communication unit 210, a motion sensor communication unit 220 for communicating with the EEG/EMG and motion detection system 130, an output control 230 for communicating with the device 150, a GPS unit 250 for determining location information, a processor 260 for performing a seizure detection determination algorithm based on EEG/EMG signals and motion sensor data detected by EEG/EMG and motion detection system 130, and a communication link 270. In some embodiments, a data storage unit 240, such as flash memory or other form of data storage component, is also provided as shown such (e.g., for storing received EEG/EMG sensor signal data and motion sensor data, such that when abnormal EEG/EMG or motor activity is detected and determined to be associated with a seizure or potential seizure event, such data can be maintained and recorded continuously for further evaluation, such as by medical or other professionals for further analysis). In some embodiments, patients/users can voluntarily and continuously record EEG/EMG and motor activity (e.g., stored on such the storage unit 240). Internal communication between components of control system 110 can be accomplished through communication link 270. In some embodiments, these functions shown and described with respect to FIG. 2 are implemented in a various other configurations, including as an integrated unit, module, or component, or as multiple distinct units, modules, or components.

In some embodiments, the output control 230 (e.g., a wireless transmission unit) transmits control signals, such as to trigger alarm or to call or notify care giver and/or doctor, and/or send various other commands. For example, if a seizure is triggered by a TV show or a movie, the output control 230 and/or the device 150 can send out a wireless signal to turn off the TV or inform the movie theater management. Once a seizure is detected, the alarm can be transmitted to allow the patient to take appropriate actions (e.g., to sit down)

before they are themselves aware that a seizure has begun. In some embodiments, treatments, such as electrical stimulation or drug injection, can also be administered to stop the evolution of the seizure. As another example, for seizures where few clinical signs are observable, tests and diagnosis can be performed more accurately if the seizure is detected earlier. In some embodiments, a programmed computer is in communication with the control system 110, and the control system 110 also includes an EEG/EMG and motion data to computer component for sending detected EEG/EMG signal samples and motion data to the computer. In this example, the computer includes a processor configured to perform a seizure detection determination algorithm based on EEG/EMG signals and motion sensor data detected by EEG/EMG and motion sensing detection system 130, and the computer can then provide the results of the analysis to the control system 110 for controlling the device 150 (e.g., based on seizure determination and/or location information). In some embodiments, the computer includes a processor configured to perform a seizure detection determination algorithm based on EEG/EMG signals and motion sensor data detected by EEG/EMG and motion detection system 130, and the computer sends corresponding control signal(s) to the device 150 based on the results of the analysis of the EEG/EMG signal samples, motion data, and/or location information (e.g., GPS data). In some embodiments, all or just a portion of the analysis of the EEG/EMG signal samples, motion data, and/or GPS data is performed by the programmed computer. In some embodiments, all or just a portion of the analysis of the EEG/EMG signal samples is performed in an EEG/EMG detection system (e.g., an ASIC integrated with or in communication with EEG/EMG sensors).

Figure 3:
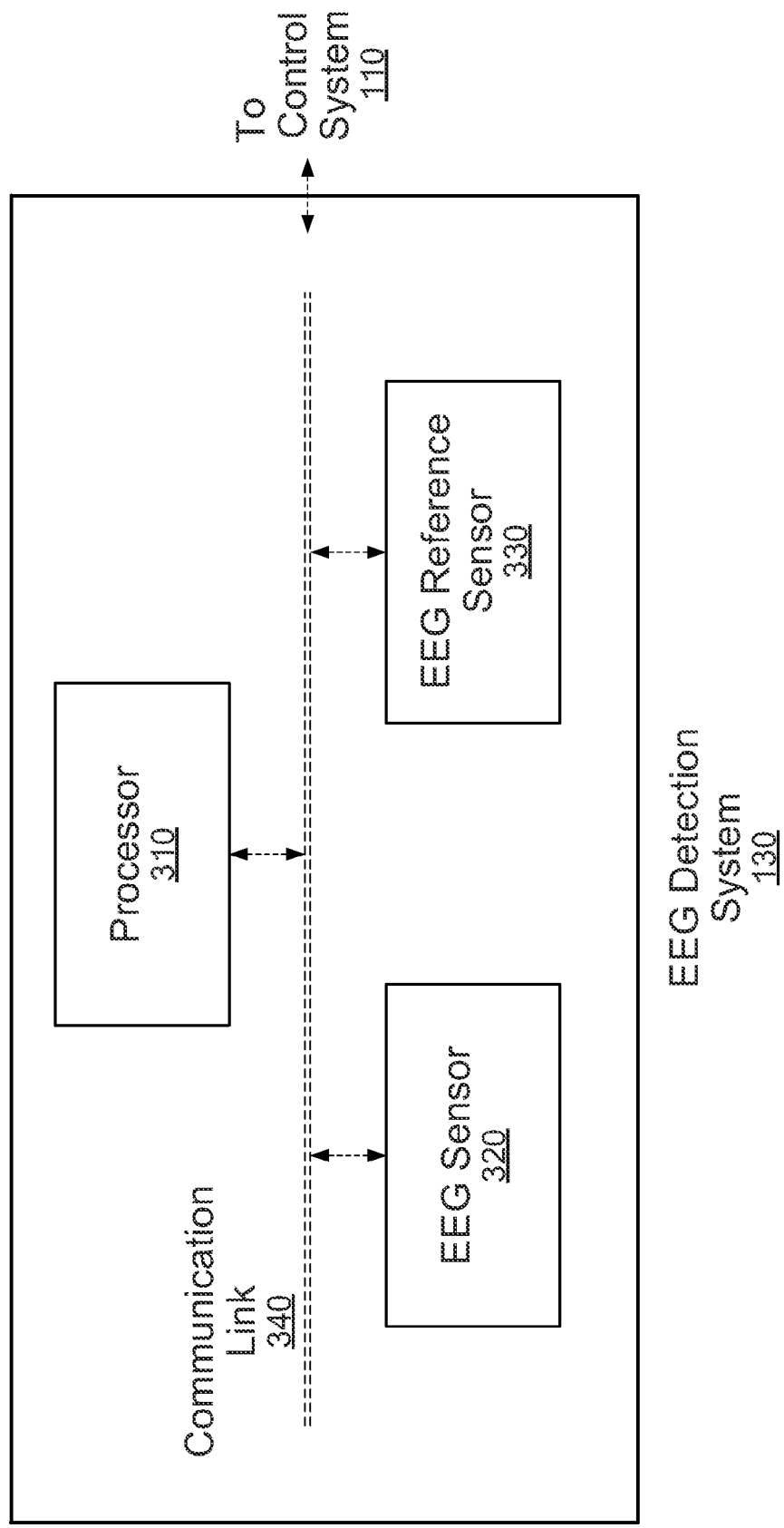
FIG. 3 is a functional diagram illustrating an EEG/EMG detection system in accordance with some embodiments.

FIG. 3 is a functional diagram illustrating an EEG/EMG detection system in accordance with some embodiments. As shown, the EEG detection system 130 includes a processor 310 (e.g., an FPGA or ASIC), active EEG sensor 320, a reference EEG sensor 330, and a communication link 340. The measured EEG signals are provided to the EEG control system 110. In some embodiments, a continuous measure of EEG signal samples are detected and provided to the control system 110.

Figure 4:
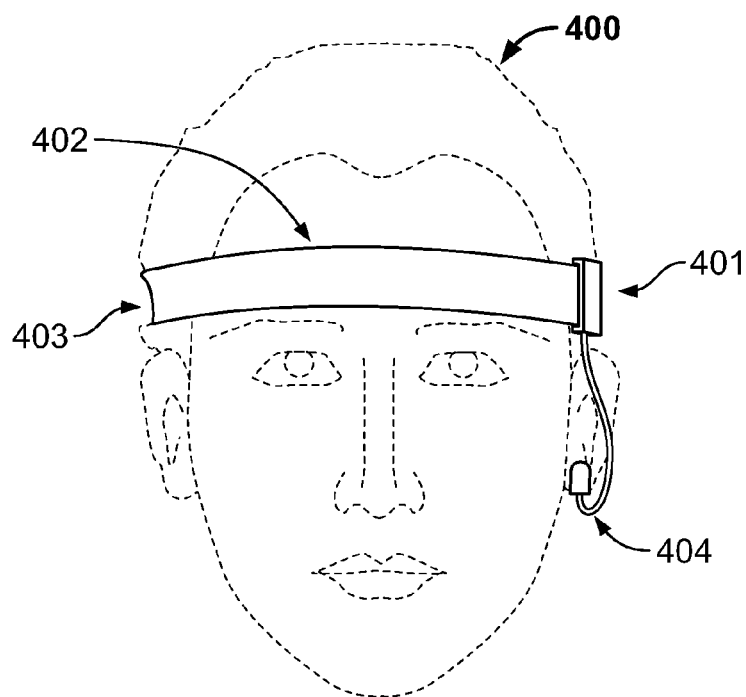
FIG. 4 is a functional diagram illustrating a seizure detection unit mounted on a headband in accordance with some embodiments.

FIG. 4 is a functional diagram illustrating an automatic seizure detection system 400 in accordance with some embodiments. As shown, a seizure detection unit 401 is mounted on a headband 403. A dry EEG sensor 402 and a reference sensor 404 are respectively mounted inside and near headband 403. In some embodiments, seizure detection system 400 includes more than one EEG sensor 402. In some embodiments, EEG sensor 402 is located in different locations based on each user's needs and/or preferences. In some embodiments, the seizure detection unit 401 is mounted on a headset, audio headset, an automobile seat headrest, and/or any other form of apparatus or module that can be used by the user to securely locate the EEG sensor(s) 402, and the reference EEG sensor 404 is mounted/provided on appropriate locations of the user's head for EEG signal detection. In some embodiments, the seizure detection system 400 includes a grounded ear clip 406 to reduce the amount of noise. In some embodiments, the seizure detection unit includes a printed circuit board (PCB) with analog front-end circuitry that amplifies the EEG signal and filters out noise. In some embodiments, the circuitry for the EEG sensor 402 is integrated into an application specific integrated circuit (ASIC). In some embodiments, a motion sensing unit 220 is included in the detection unit 401 to measure the user's movement (e.g., in real-time). In some embodiments, the detection unit 401 includes a microprocessor 260 to sample the EEG and/or motion data at predefined sampling rates and to determine if the user/patient is having a seizure. In some embodiments, the detection unit 401 also includes a memory 240 to store data. In some embodiments, the detection unit 401 also includes a wireless transmission unit 230 to communicate/wirelessly transmit and/or receive information (e.g., data, alerts, and commands and/or other information). In some embodiments, the detection unit 401 also includes a GPS sensor 250 to record/store location information of the user/patient when a seizure event is determined and/or to communicate location information of the user/patient when a seizure event is determined, such as by the wireless transmission unit 230.

Figure 5:
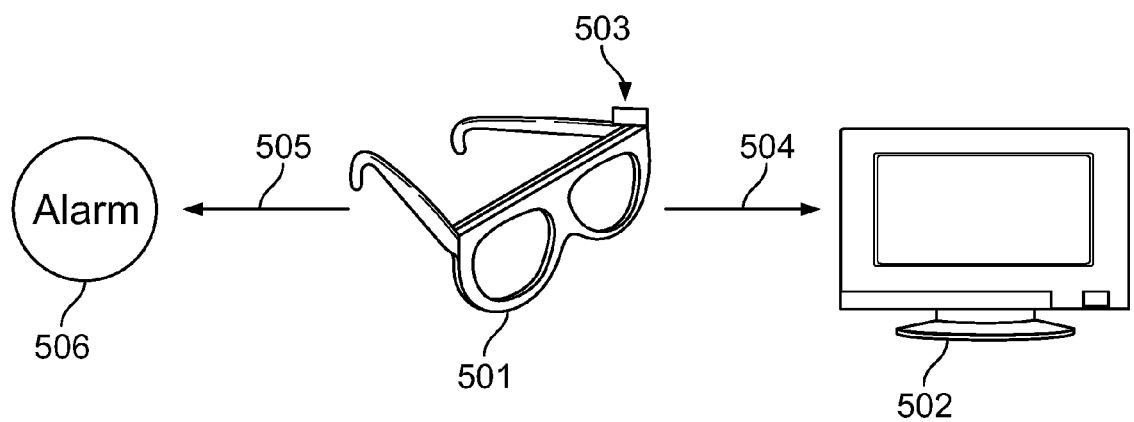
FIG. 5 is a functional diagram illustrating a seizure detection unit mounted on a pair of 3D glasses in accordance with some embodiments.

FIG. 5 is a functional diagram illustrating a seizure detection unit mounted on a pair of 3D glasses 501 in accordance with some embodiments. As shown, the seizure detection unit 503 is mounted on 3D glasses 501. In some embodiments, the seizure detection unit includes a microprocessor 260 that processes the EEG/EMG and/or motor activity and determines if the user/patient is having a seizure. For example, if a seizure is detected, one or both eyes can be covered by the glasses 501 (e.g., automatically darkening one or more of the lenses of the glasses). In some embodiments, a wireless transmission unit 230 is provided such that a signal 504 is sent to the display 502 (e.g., a computer with a integrated or connected display device/element, television, a mobile entertainment device, PDA/smartphone device, and/or another display device) from the seizure detection unit 503 to stop the visual stimulation. In some embodiments, a wireless signal 505 is sent to the alarm 506 by the seizure detection unit 503. In some embodiments, a headband (e.g., or headset) and glasses can be combined together to mount a seizure detection unit.

In some embodiments, the seizure detection control device 110 includes a motion sensing device 220. If abnormal activities are detected (e.g., a potential seizure or seizure event are determined), one or both eyes of glasses 501 can be covered to eliminate or reduce the visual stimulation to the patient. In some 3D glasses (e.g., active shutter glasses), glasses 501 are controlled by a transmitter that sends a timing signal 404 that allows the glasses to alternately darken over one eye, and then the other, in synchronization with the refresh rate of screen 502. In some embodiments, if a seizure is detected, the transmitter controls one or both eyes' glasses to be dark continuously. In some embodiments, an alarm signal 506 can be transmitted, and/or the device that triggered the seizure can be disabled or powered off.

Figure 6:
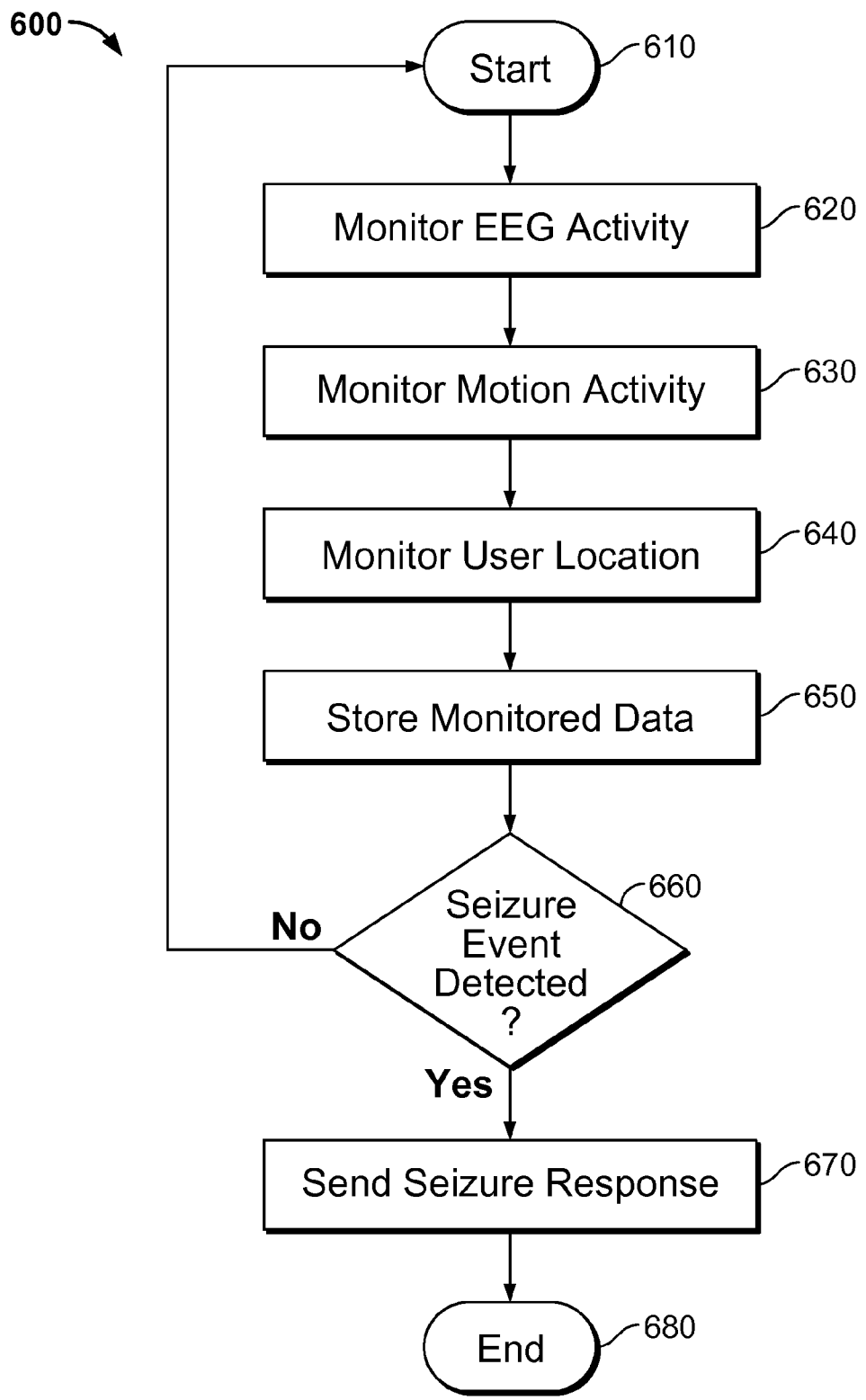
FIG. 6 is a flow diagram for techniques seizure detection and monitoring techniques in accordance with some embodiments.

FIG. 6 is a flow diagram for seizure detection and monitoring techniques in accordance with some embodiments. It is understood that not all steps of process 600 as shown in FIG. 6 are required in order to realize seizure detection and response. It is also understood that the steps of the process 600 may be arranged in any order and in any repetition. As shown, the process begins at 610. In some embodiments, the occurrence of seizures can be detected if excessive or synchronous EEG/EMG activity is detected at 620. Various EEG/EMG patterns, such as sustained rhythmic activity, increase in amplitude, or EEG flattening can indicate the happening seizures. For example, a detection algorithm can be based on one or more features computed from spectral or wavelet decomposition, amplitude or power change in relative to background activity, and/or a template method. These features can be combined in a classifier such as a linear discrimination analysis, an artificial neural network, a decision tree, or a Bayesian method to determine the occurrence of seizures.

In some embodiments, the occurrence of seizures can also be detected by abnormal motor activity recorded from motion sensing unit 220 at 630. For example, the motion of an object can be detected by measuring change in speed or direction of that object in relative to its environment. An accelerometer is one type of motion sensor that measures the proper acceleration of the device. In some embodiments, piezoelectric, piezoresistive and/or capacitive accelerometers can be used to measure the motor activity of users.

Examples of motor symptoms of seizures include muscle jerking and stiffening. Involuntary but coordinated movements, such as smacking, chewing, fidgeting and walking can also happen during seizures. Some patients lose consciousness and fall during seizure, so abrupt body movements also occur. Various movement patterns, such as sustained rhythmic activity and sudden change in velocity, can indicate the occurrence of seizures. In some embodiments, a seizure detection algorithm is based on one or more features computed from spectral or wavelet decomposition, amplitude or power change in relative to background velocity, and/or a template method. For example, these features can be combined in a classifier, such as a linear discrimination analysis, an artificial neural network, a decision tree, or a Bayesian method to determine the occurrence of seizures.

In some embodiments, a GPS sensor or other locating system may, at step 640, record/store location information of the user/patient when a seizure event is determined and/or to communicate location information of the user/patient at step 670 when a seizure event is determined (e.g., using the wireless transmission unit 230).

At 650, monitored EEG/EMG sensor data, motion data, and location data are stored. At 660, based on the monitored EEG/EMG sensor data and motion data, whether a seizure event has been detected is determined. If a seizure response is determined to have been detected, then a seizure response can be performed at 670. Otherwise, the process returns to 610 as shown. In some embodiments, the process ends at 680.

In some embodiments, a detection algorithm is embedded in the recording unit and makes decisions in real-time at step 660. In some embodiments, the EEG/EMG and motion data are transmitted wirelessly to another device 150 or functional element (e.g., a computer or another computing or processing device) where the decision is made at step 660 and proper actions are taken at step 670.

In some embodiments, the occurrence of seizures is detected at step 660 by combining information recorded from EEG/EMG and motion sensing units, such as using the various techniques described herein and/or other similar or related techniques as would now be apparent to one of ordinary skill in the art. For example, features from EEG/EMG and motor activities can be combined in a classifier, such as a linear discrimination analysis, an artificial neural network, a decision tree, or a Bayesian method to determine the occurrence of seizures.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. An apparatus for detecting and monitoring a seizure, the apparatus comprising:
   one or more dry electroencephalography (EEG) sensors or electromyography (EMG) sensors mounted on a wearable object;
   a motion sensor mounted on the wearable object;
   a detection unit configured to determine occurrence of a seizure event based on data received from the EEG or EMG sensor and the motion sensor, wherein the determining of the occurrence of the seizure event comprises:
      receive a first data from the EEG or EMG sensor and receive a second data from the motion sensor; and
      determine the occurrence of the seizure event based on an analysis of one or more features from the first data and the second data using a classifier, wherein the classifier comprises a linear discrimination analysis, an artificial neural network, a decision tree, or a Bayesian method; and
   a transmission unit configured to send a seizure response, wherein the seizure response comprises administering treatment to a user of the apparatus.

2. The apparatus according to claim 1, further comprising a storage unit, wherein the storage unit is capable of recording seizure event data and non-seizure event data from the detection unit.

3. The apparatus according to claim 1, further comprising a location tracking unit.

4. The apparatus according to claim 1, wherein the wearable object is a headband.

5. The apparatus according to claim 1, wherein the wearable object is a pair of glasses or a pair of active-lens 3D glasses.

6. The apparatus according to claim 5, wherein the seizure response further comprises commanding at least one lens of the 3D glasses to modify a timing for darkening.

7. The apparatus according to claim 1, wherein the seizure response further comprises a trigger alarm to the user or a third party.

8. The apparatus according to claim 1, wherein the seizure response further comprises commanding a device producing visual stimulus to modify its behavior.

9. The apparatus according to claim 1, wherein the determining of the occurrence of the seizure event further comprises:
   determine whether the first data received from the EEG or EMG sensor includes a sustained rhythmic activity, an increase in amplitude, an EEG flattening, or any combination thereof; and
   in the event that the first data received from the EEG or EMG sensor includes the sustained rhythmic activity, the increase in amplitude, the EEG flattening, or any combination thereof, determine the occurrence of the seizure event.

10. The apparatus according to claim 9, wherein the user wearing the wearable object is standing or sitting up.

11. The apparatus according to claim 1, wherein the determining of the occurrence of the seizure event further comprises:
   determine whether the second data received from the monitored motor activity relates to a change in speed or a change in direction relative to environment exceeding a predetermined threshold; and
   in the event that the change in speed or the change in direction relative to environment exceeds the predetermined threshold, determine the occurrence of the seizure event, the user wearing the wearable object being in an orientation other than lying horizontal.

12. The apparatus according to claim 1, wherein the one or more features are combined in the classifier, and wherein the one or more features are computed from one or more of the following: spectral or wavelet decomposition, amplitude or power change in relative to background activity, and a template method.

13. A method for detecting and monitoring a seizure, the method comprising:
- monitoring electroencephalography (EEG) or electromyography (EMG) activity of a user through a wearable object that includes one or more dry EEG sensors or EMG sensors;
- monitoring motor activity of the user through the wearable object that includes a motion sensor;
- determining occurrence of a seizure event based on data received from the monitored EEG or EMG activity and the monitored motor activity, wherein the determining of the occurrence of the seizure event comprises:
  - receiving a first data from the monitored EEG or EMG activity and receiving a second data from the monitored motor activity; and
  - determining the occurrence of the seizure event based on an analysis of one or more features from the first data and the second data using a classifier, wherein the classifier comprises a linear discrimination analysis, an artificial neural network, a decision tree, or a Bayesian method; and
- responding automatically to the seizure event, wherein the responding comprises administering treatment to the user.

14. The method according to claim 13, further comprising recording at least one of seizure event data and non-seizure event data.

15. The method according to claim 13, further comprising tracking the user's location.

16. The method according to claim 13, wherein the wearable object is a headband, a pair of glasses, or a pair of active-lens 3D glasses.

17. The method according to claim 16, wherein the responding further comprises commanding at least one lens of the 3D glasses to modify a timing for darkening.

18. The method according to claim 13, wherein the responding further comprises commanding a device producing visual stimulus to modify its behavior.

19. The method according to claim 13, wherein the determining of the occurrence of the seizure event further comprises:
- determining whether the first data received from the EEG or EMG sensor includes a sustained rhythmic activity, an increase in amplitude, an EEG flattening, or any combination thereof; and
- in the event that the first data received from the EEG or EMG sensor includes the sustained rhythmic activity, the increase in amplitude, the EEG flattening, or any combination thereof, determining the occurrence of the seizure event.

20. The method according to claim 19, wherein the user wearing the wearable object is standing or sitting up.

21. The method according to claim 13, wherein the determining of the occurrence of the seizure event further comprises:
- determining whether the second data received from the monitored motor activity relates to a change in speed or a change in direction relative to environment exceeding a predetermined threshold; and
- in the event that the change in speed or the change in direction relative to environment exceeds the predetermined threshold, determining the occurrence of the seizure event, the user wearing the wearable object being in an orientation other than lying horizontal.

22. The method according to claim 13, wherein the one or more features are combined in the classifier, and wherein the one or more features are computed from one or more of the following: spectral or wavelet decomposition, amplitude or power change in relative to background activity, and a template method.

23. The method according to claim 13, wherein the responding further comprises triggering an alarm communicated to the user or a third party.

* * * * *